United States Patent
Rhee

(10) Patent No.: US 6,206,821 B1
(45) Date of Patent: Mar. 27, 2001

(54) DEVICE FOR GENERATING, RECORDING AND REPRODUCING BRAIN WAVE SOUND AND FETAL VITAL SOUND FOR A WOMAN AND HER FETUS

(75) Inventor: Young Deuck Rhee, Kyungki-do (KR)

(73) Assignee: Daeyang E & C, Seoul (KR)

( * ) Notice: Subject to any disclaimer, the term of this patent is extended or adjusted under 35 U.S.C. 154(b) by 0 days.

(21) Appl. No.: 09/433,237

(22) Filed: Nov. 4, 1999

(30) Foreign Application Priority Data

Mar. 12, 1999 (KR) .................................................. 99-8386

(51) Int. Cl.$^7$ ............................. A61M 21/00; A61B 5/05; A61B 5/02
(52) U.S. Cl. ................................. 600/28; 600/26; 600/27; 600/545; 600/528
(58) Field of Search ..................................... 600/545, 544, 600/528, 527, 508, 300, 26, 28, 27

(56) References Cited

U.S. PATENT DOCUMENTS

| | | | |
|---|---|---|---|
| 4,898,179 | * | 2/1990 | Sirota ................................... 600/483 |
| 4,934,998 | * | 6/1990 | Thomas, Jr. ........................... 600/27 |
| 5,063,912 | * | 11/1991 | Hughes ................................. 600/47 |
| 5,109,421 | * | 4/1992 | Fox ....................................... 381/90 |
| 5,491,756 | * | 2/1996 | Francais ................................ 381/90 |
| 5,764,776 | * | 6/1998 | Francais ................................ 381/124 |
| 5,913,834 | * | 6/1999 | Francais ................................ 600/591 |

* cited by examiner

*Primary Examiner*—Cary O'Connor
*Assistant Examiner*—Navin Natnithithadha
(74) *Attorney, Agent, or Firm*—Staas & Halsey LLP

(57) ABSTRACT

Disclosed is an antenatal training device for a pregnant woman comprising: a fetal vital sound generating unit for collecting and outputting a signal representative of a fetal vital sound generated to correspond to the detected heartbeats and movement of a fetus; and a brain wave sound generating unit connected to the fetal vital sound generating unit, for generating a brain wave frequency signal generated in the most stable and comfortable state of the body and mind among various brain waves of the human body, modulating it with an audio frequency signal, mixing the modulated brain wave sound signal and the fetal vital sound signal, and amplifying the mixed brain wave sound and fetal vital sound signals for application to an audio output part, thereby allowing a user to hear them which in turn induces the user to a psychologically serene state or a relaxing state. This device has assistant antenatal training effects in that while a pregnant woman is hearing the brain wave sound such as an alpha ($\alpha$) wave along with the fetal vital sound, she can be induced into a psychologically serene state or a relaxing state promoting the growth of a fetus while causing an emotional stability of a fetus.

7 Claims, 2 Drawing Sheets

DEVICE FOR GENERATING, RECORDING AND REPRODUCING BRAIN WAVE SOUND AND FETAL VITAL SOUND FOR A WOMAN AND HER FETUS

BACKGROUND OF THE INVENTION

1. Field of the Invention

The present invention relates to an antenatal training device, and more particularly to a device which releases psychological and physiological stress and tension of a pregnant woman by stimulating her senses of hearing, and in turn induces the woman and her fetus to a mentally serene state during a gestation period.

2. Description of the Related Art

In general, all living individuals generate brain waves as kind of vital waves. Such brain waves represent different frequencies in accordance with an awakening state or a degree of a mental stability, and various devices employing this variation in frequency have been developed. Typically, a medical appliance for diagnosis and a lie detector utilizing a variation in brain wave frequency have already been put to practical use, and especially a device for promoting learning effects by creating a psychological serenity has also been developed.

Brain waves are accompanied with a sort of variation in voltage generated rhythmically from a brain part of a human body, which has frequencies of approximately 1 to 60 Hz and voltages of approximately 10 to 100 $\mu V$. Such brain waves are divided into a $\delta$ (delta) wave, an $\alpha$ (alpha) wave, a $\delta$ (beta) wave in the lower order of a frequency band range. It has been found that the $\alpha$ (alpha) wave of frequencies of 7 to 11 Hz among various brain waves is generated in a condition of the human mind and body being under a stable, comfortable and relaxing state.

In U.S. Pat. No. 4,898,179, dated Feb. 6, 1990, entitled "Device for Detecting, Monitoring, Displaying and Recording of Material and Fetal Vital Signs and Permitting Communication between a Woman and Her Fetus," there is provided a device for detecting, monitoring, displaying and recording a representation of the heartbeats of a pregnant woman and her fetus. In this prior art device, signals representative of heartbeats and movements of the fetus detected can be recorded for later playback. Also, a microphone and speaker permit a woman to provide an audio stimulation to the fetus (or so called fetal child), and the fetal response to this stimulation can then be monitored.

However, the above-mentioned device allows the woman to provide an audio stimulation to the fetal child, and in particular, replies on only signals representing the heartbeats, thereby causing a failure in an antenatal training through mental and emotional stability of the pregnant woman's herself. Particularly, considering that mental and emotional stability of the pregnant woman is essential for psychological and emotional development of the fetus during a gestation period, the above-mentioned U.S. Patent has a relatively very limited aspect in view of a device for assisting in antenatal training.

SUMMARY OF THE INVENTION

In view of the above, therefore, it is an object of the present invention to provide an antenatal training device for a pregnant woman including a fetal heart sound generating unit which can generate artificially the same wave as the specific brain wave which makes it possible for the body and mind to be the most stable and comfortable among various brain waves generated from the human body, tune it with the current actual brain wave frequency generated therefrom, and output an audio frequency signal to a pregnant woman, thereby not only inducing her to a psychologically serene state or a relaxing state but also greatly aiding in formation of fetus's character in accordance with her mental stability.

It is another object of the invention to provide an antenatal training device for a pregnant woman including a fetal vital sound generating unit which can record an artificially generated brain wave signal for imparting to a pregnant woman as well as a signal representative of heartbeats and movements of her fetus detected, thereby allowing the woman to later selectively reproduce and hear them, if desired.

In an aspect of the present invention, there is provided an antenatal training device for a pregnant woman comprising: a fetal vital sound generating means for collecting and outputting a signal representative of fetal vital sound including detected sound generated from heartbeats and movements of a fetus; and a brain wave sound generating means connected to the fetal vital sound generating means, for generating a brain wave frequency signal generated in a stable and comfortable state of the human body and minds and outputting mixed sound of the fetal vital sound and the brain wave sound.

In accordance with the present invention, an antenatal training device comprises a terminal for converting the generated brain wave sound and collected fetal vital sound to an electrical signal and outputting the converted electrical signal to an exterior recording/reproducing unit which allows a user to hear the desired brain wave sound and the fetal vital sound, if desired.

In the present invention, built-in recording/reproducing functions permit a user to selectively hear the desired brain wave sound and the fetal vital sound, if desired.

BRIEF DESCRIPTION OF THE DRAWINGS

The foregoing and other objects, features and advantages of the present invention will become more apparent from the following detailed description when taken in conjunction with the accompanying drawings in which.

DETAILED DESCRIPTION OF THE PREFERRED EMBODIMENT

Reference will now be made in detail to the preferred embodiments of the present invention. In the following description of the present invention, a detailed description of known functions and configurations incorporated herein will be omitted when it may make the subject matter of the present invention rather unclear.

Figure 1:
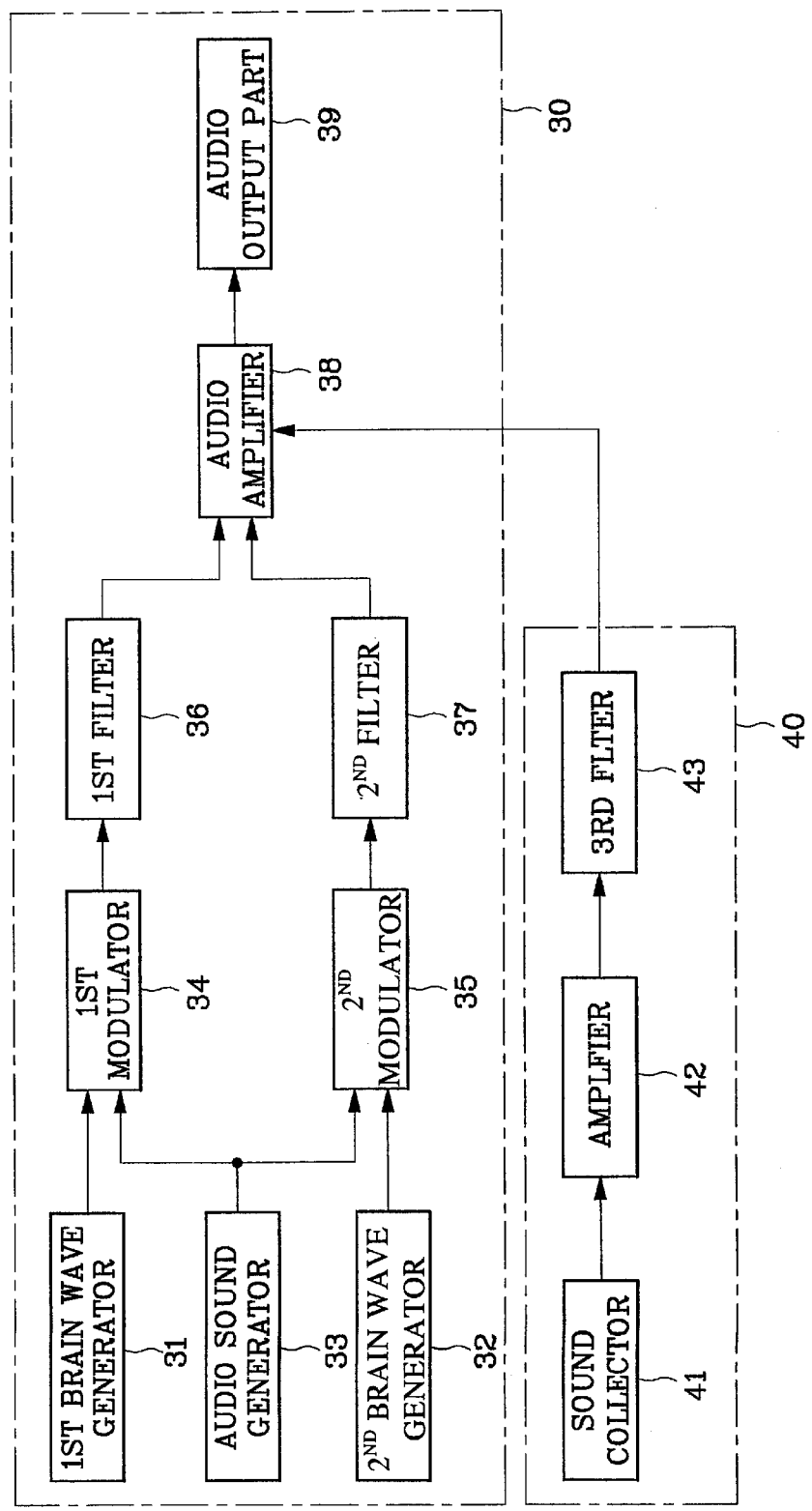
FIG. 1 is a block diagram illustrating a construction of an antenatal training device to which a fetal vital sound generating unit is mounted in accordance with a first preferred embodiment of the present invention.

FIG. 1 illustrates a construction of an antenatal training device to which a fetal heart sound generating unit is mounted in accordance with a first preferred embodiment of the present invention.

Referring to FIG. 1, the antenatal training device for a pregnant woman comprises a brain wave sound generating unit 30 and a fetal vital sound generating unit 40. The brain wave sound generating unit 30 is adapted to artificially generate a brain wave frequency corresponding to a brain wave, i.e. an alpha (α) wave generated in the most stable and comfortable state of the body and mind among various brain waves of the human body, and modulate the generated brain wave frequency to an audio frequency signal for allowing a user to hear it. The fetal vital sound generating unit 40 is adapted to collect and output signals representative of fetal vital sounds generated to correspond to heartbeats and movements of a fetus detected.

The brain wave sound generating unit 30 is provided with a first brain wave generator 31, a second brain wave generator 32, and an audible sound generator 33. The first brain wave generator 31 operates to oscillate an extremely low frequency of 7 to 11 Hz to artificially generate the alpha (α) wave, i.e. a first brain wave, and a second brain wave generator 32 serves to generate a second brain wave having a phase identical to that of the brain wave generated by the first brain wave generator 31 or a phase opposite thereto in order to maximize tuning effects of brain waves. The audible sound generator 33 is adapted to generate a sound of the frequency band which is audible to an ear. Because the generated first and second brain waves, which are low frequencies, are not audible to an ear, they are modulated along with frequencies of the audible sounds generated from the audible sound generator 33, respectively, in a first modulator 34 and a second modulator 35.

That is, the first modulator 34 is operative to modulate a frequency of the first brain wave signal from the first brain wave generator 31 along with and a frequency of an audible sound from the audible sound generator 33, and the second modulator 35 is operative to modulate a frequency of the second brain wave signal from the second brain wave generator 32 along with a frequency of the audible sound from the audible sound generator 33. The modulated first and second brain wave signals generated from the first and second modulators 34 and 35 are supplied to a first filter 36 and a second filter 37, respectively.

Namely, the first modulator 34 generates a baseband signal, and the second modulator 35 generates a baseband signal. Because the modulated brain wave signals generated from the first and second modulator 34 and 35 are of baseband levels, the first and second filters 36 and 37 are comprised of low pass filters rather than bandpass filters. The first and second low pass filters 36 and 37 are operative to pass, with minimal attenuation, frequency components of the baseband signal up to a low pass filter cutoff frequency, for example, of 1,000 Hz, and then to reject frequency components of other baseband signals above the low pass filter cutoff frequency to remove undesired noises. The first and second filters 36 and 37 generate filtered audio frequency signals which are coupled to an audio amplifier 38. The audio amplifier 38 is adapted to amplify the filtered weak audio frequency signals before outputting them to the outside through an audio output part 39 or a transducer, such as a speaker.

Meanwhile, fetal vital sound, which is indicative of a sound generated to correspond to the detected heartbeats or movement of a fetus detected, is collected by a sound collector 43 located for juxtaposition to a part of a pregnant woman's body, i.e. her abdomen and in proximity to the fetus. The sound collector 41 generates a signal representative of the collected fetal vital sound which is applied to an amplifier 42. The amplifier 42 amplifies the collected fetal vital sound signal for application to a third filter 43. The third filter 43 generates a filtered fetal vital sound signal which is applied to the audio amplifier 38. At this time, the third filter 43 is operative to pass frequency components of the baseband signal up to the detected heartbeat frequency, for example, of 120 Hz, and then to reject frequency components of other baseband signals above the detected heartbeat frequency to remove undesired noises.

Like this, the audio amplifier 38 amplifies the filtered weak audio frequency signals each generated from the first and second filters 36 and 37 along with a filtered signal representative of the fetal vital sound outputted from the fetal vital sound generating unit 40 to a stereo signal, which is applied to an audio output 39 for outputting it as a sound to the outside. A conventional stereo speaker may be used to output an audio sound, and the use of an output terminal such as a jack allows a user or a pregnant woman to hear the audio sound through a headphone or an earphone.

As can seen from the foregoing, a pregnant woman can hear a combined sound of the brain wave sound and the fetal vital sound while hearing directly a vital sound of a her fetus along with the tuned brain wave sound, thereby allowing the woman to be induced into a psychologically and emotionally serene state or a relaxing state, which in turn greatly helps her fetus to be in mental and emotional stability. In addition, the audible sound generator 33 is operative to generate an audio frequency of 100 to 500 Hz. As a result, a user can select a desired sound in accordance with user's own preference.

Figure 2:
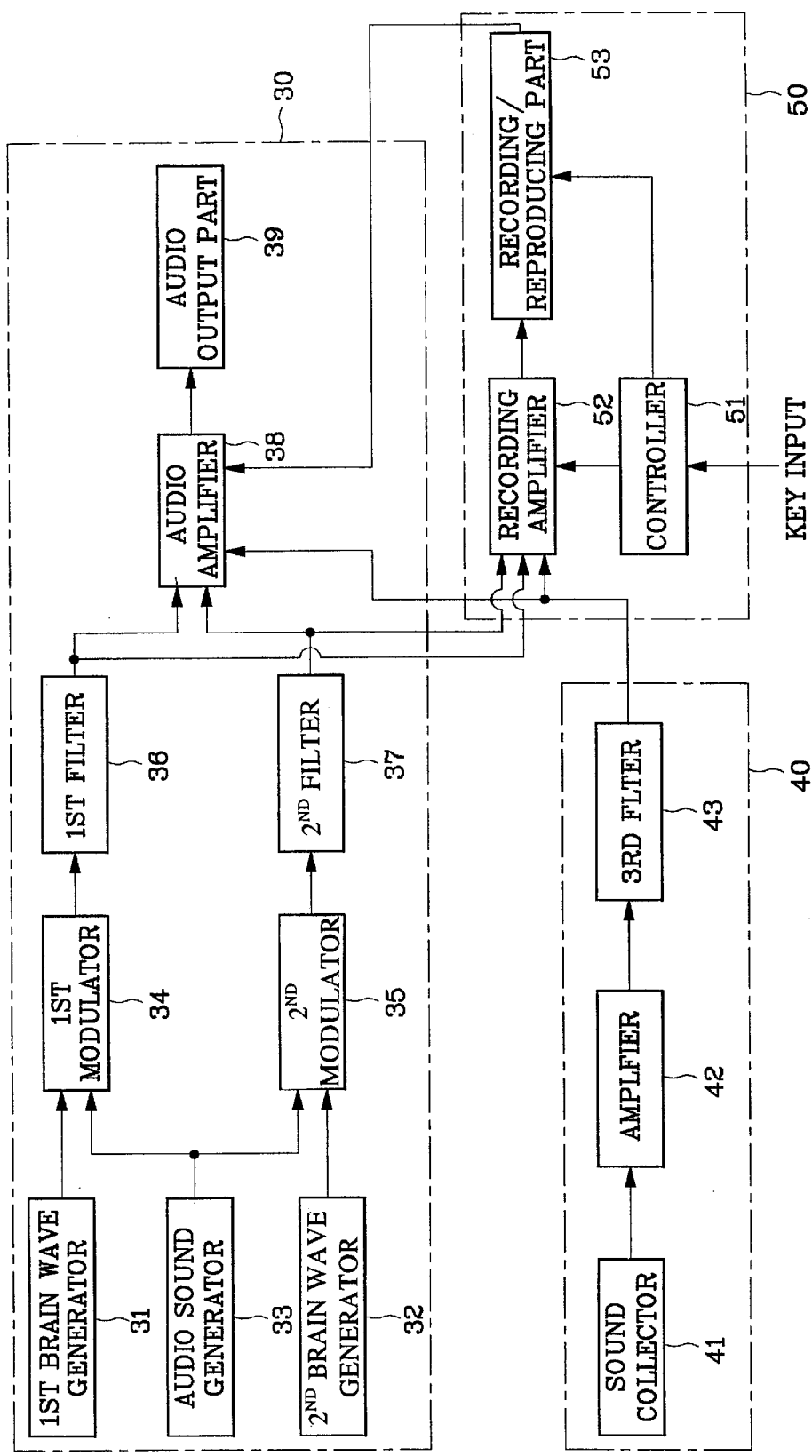
FIG. 2 is a block diagram showing a construction of an antenatal training device to which a fetal vital sound generating unit is mounted in accordance with a second preferred embodiment of the present invention.

FIG. 2 illustrates a construction of an antenatal training device in accordance with another preferred embodiment of the present invention.

In FIG. 2, it is noted that the same reference numerals or letters will be used to designate like or equivalent elements having the same function as in construction of the present invention shown in FIG. 1. The detailed description on known functions and constructions unnecessarily obscuring the subject matter of the present invention will be avoided hereinafter.

Referring to FIG. 2, a brain wave generating unit 30 and a fetal vital sound generating unit 40 have the same construction as shown in FIG. 1, but have an additional recording/reproducing function by which the brain wave sound of an alpha (α) wave frequency and the fetal vital sound can be recorded for later playback, thereby allowing a user to hear them at any time if desired.

Accordingly, unlike the antenatal training device in FIG. 1 which permits a user or a pregnant woman to directly hear at a real time a fetal vital sound or an audio signal generated to correspond to the detected heartbeats and movements of a fetus, the antenatal training device in FIG. 2 allows a user to reproduce and hear the fetal vital sound which had been recorded in an energetic movement of the fetus even in a state in which a fetal child is sleeping or is rather sluggish in movement. Also, when a user wants to hear the recorded fetal vital sound, the user can hear repeatedly it along with the brain wave sound of an alpha (α) wave frequency at any time.

For the purpose of this, in addition to the brain wave generating unit 30 and a fetal vital sound generating unit 40, the antenatal training device in FIG. 2 further comprises a recording/reproducing unit which consists of a recording/reproducing section 53, an amplifier 52 for recording, and a controller 51 for controlling the overall operations of the recording/reproducing section 53 and the amplifier 52. The amplifier 52 amplifies the brain wave sound or the filtered weak audio frequency signal generated from the first and second filters 36 and 37, and the filtered fetal vital sound signal outputted from the third filter 43 to a predetermined signal level for application to a recording/reproducing section 53 which stores the amplified audio signal on a recording media therein.

A conventional memory device including a magnetic tape, a diskette, a disk, a flash memory, RAM (Random Access Memory), EPROM, and EEPROM, etc. may usually be used as a recording media. Preferably, a non-volatile memory is used which can continue to maintain the stored data (signals) even in case that a supply of electric power is stopped. Based on a type of these memory units, a device for driving these memory means and a controller may be structured in accordance with a conventional method.

The recording/reproducing unit 50 is always provided with a key (button) indicating start and end of a recording operation, and start and end of a reproducing (playback) operation for a user. When there is a key input for executing a recording or a reproducing operation mode, the controller 51 serves to control the recording or reproducing operation of the brain wave sound and the fetal vital sound. The collected, amplified, and filtered fetal vital sound signal generated from the fetal vital sound generating unit 40 is simultaneously applied to the audio amplifier 38 and the amplifier 52 for recording so that a user or a pregnant woman can hear directly the fetal vital sound signal applied to the audio amplifier 38 or record the fetal vital sound signal applied to the amplifier 52 through the recording/reproducing section 53 in accordance with a key input of the user.

In addition, the filtered audio frequency signal generated from the first and second filters 36 and 37 which is preceded by generating the first and second brain wave signals from the first and second brain wave generator 31 and 32 and modulating them with the audible sound signal from the audible sound generator 31, is also applied to the audio amplifier 38 for audio output while being also applied to the amplifier 52 so that a user can record the filtered audio frequency signal applied to the amplifier 52 through the recording/reproducing section 53 in accordance with a key input of the user. Further, the audio frequency signal recorded in the recording/reproducing section 53 can be reproduced by a user at any time to hear it through a speaker or a headphone.

Although the recording/reproducing unit 50 has been described in its preferred form with the particular construction in which it is embedded in the antenatal training device of the present invention, it is to be understood that it employs a system designed for transferring a signal to communicate with a conventional cassette player, etc. if desired, and a user can record the fetal vital deep signal through a recording apparatus such as an exterior independent cassette player or a computer having a recording function by signal transmission via a cable.

In this case, the built-in recording media or the recording/reproducing unit 50 in which the brain wave sound signal and the fetal vital sound signal are stored may be replaced with an exterior recording/reproducing unit, and the sound signals can be outputted as an audio signal by connecting the exterior recording/reproducing unit to the antenatal training device of the present invention.

Turning now to FIG. 2, an explanation on the overall operation of an antenatal training device to which the brain wave generating unit 30, the fetal vital sound generating unit 40 and the recording/reproducing unit 50 are coupled will be in detail given hereinafter.

First of all, while a user or a pregnant woman is hearing the brain wave sound and the fetal vital sound including heartbeats or movement of her fetus generated through working of the brain wave generating unit 30 and the fetal vital sound generating unit 40, the woman can record the brain wave sound and the fetal vital sound for later playback by means of the recording/reproducing unit 50.

That is, when the woman presses a recording key of a key input part mounted to one side of the recording/reproducing unit 50, the controller 51 generates a driving control signal for driving the amplifier 52 in response to an input signal of the recording key while generating a recording control signal for application to the recording/reproducing section 53. As a result, a driving mode of the recording/reproducing section 53 is shifted from a stop mode to a recording mode.

Therefore, the amplifier 52 amplifies the brain wave sound signal, i.e., the filtered weak audio frequency signal generated from the first and second filters 36 and 37 in the brain wave sound generating unit 30, and the filtered fetal vital sound signal including the heartbeats or movement of a fetal child generated from the third filter 43 in the fetal vital sound generating unit 40 to a predetermined signal level for application to the recording/reproducing section 53 to record them on a recording media thereof. Consequently, the recording/reproducing section 53 allows the amplified brain wave sound signal and fetal vital sound signal generated from the amplifier 52 to be recorded on the recording media.

When the user presses a playback key of the key input part in order to hear again the brain wave sound signal and fetal vital sound signal recorded on the recording media of the recording/reproducing section 53 after the user or pregnant woman has recorded, the controller 51 generates a driving control signal for driving the amplifier 52 in response to an input signal of the playback key while generating a reproducing control signal for application to the recording/reproducing section 53. As a result, the driving mode of the recording/reproducing section 53 is in turn shifted from a stop mode to a reproducing mode.

At this time, the recording/reproducing section 53 reproduces the brain wave sound signal and fetal vital sound signal recorded on the recording media for application to the audio amplifier 38 in the brain wave sound generating unit 30 in response to the reproducing control signal outputted from the controller 51. The audio amplifier 38 amplifies the reproduced brain wave sound signal and fetal vital sound signal outputted from the recording/reproducing section 53 to a stereo audio signal which is applied to the audio output part 39, i.e. a stereo headphone for outputting to an ear of the pregnant woman.

In addition, the antenatal training device in accordance with the present invention is provided with a key pad or a set of buttons as an input means for a user, and an input signal of the key supplied to the controller 51 allows the overall operation of the device to be controlled. Preferably, the device further comprises a LCD display (not shown) coupled to the controller 51 in order to display the current operating state of the device.

As described above, an antenatal training device for a pregnant woman including a fetal vital sound generating unit in accordance with the instant invention permits generating artificially a brain wave, i.e. an alpha ($\alpha$) wave having a frequency of about 7 to 11 Hz generated in the most stable and comfortable state of the body and mind among various brain waves of the human body, modulating it with an audio frequency signal, and generating a fetal vital sound including detected heartbeats or movements of a fetus along with the brain wave sound for application to an audio output part, thereby allowing a user, particularly a pregnant woman to hear them at any time. Further, the device in accordance with the this invention makes it possible for the user to record both the brain wave sound and the fetal vital sound, and then reproduce the recorded brain wave sound and the fetal vital sound to hear again later, if desired.

As can be seen from the foregoing, the device in accordance with the present invention has assistant antenatal training effects in that while a pregnant woman is hearing the brain wave sound such as an alpha (α) wave along with the fetal vital sound, the woman can be induced into a psychologically serene state or a relaxing state, which in turn promotes the growth of a fetus and causes emotional stability of a fetus. The device of the present invention has mainly been designed for a pregnant woman, but is also effective to adult men, women, children, and psychopathic patients.

In accordance with the present invention, the inventive antenatal training device may further comprises a terminal for converting the generated brain wave sound and collected fetal vital sounds to an electrical signal and outputting the converted electrical signal to an exterior recording/reproducing unit which allows a user to hear the desired brain wave sound and the fetal vital sounds, if desired.

While this invention has been described in connection with what is presently considered to be the most practical and preferred embodiment, it should be understood that the invention is not limited to the disclosed embodiment, but, on the contrary, it is intended to include and cover variations, modifications and substitutions within the spirit and scope of the appended claims.

What is claimed is:

1. An antenatal training device for a pregnant woman comprising:
   a fetal vital sound generating means for collecting and outputting a signal representative of fetal vital sound including detected sound generated from heartbeats and movements of a fetus; and
   a brain wave sound generating means connected to the fetal vital sound generating means, for generating a brain wave frequency signal generated in a stable and comfortable state of the human body and mind, and outputting mixed sound of the fetal vital sound and the brain wave sound.

2. The device of claim 1, wherein the brain wave sound generating means comprises:
   a first brain wave generator for generating the same first brain wave signal having a low frequency as an alpha (α) wave;
   a second brain wave generator for generating a second brain wave having a phase identical to that of a brain wave generated the first brain wave generator or a phase opposite thereto in order to maximize tuning effects of brain waves;
   an audible sound generator for generating an audible frequency signal;
   a first modulator connected with the first brain wave generator and the audible sound generator, for modulating a frequency of the first brain wave signal generated from the first brain wave generator along with a frequency of the audible sound signal generated from the audible sound generator;
   a second modulator connected with the second brain wave generator and the audible sound generator, for modulating a frequency of the second brain wave signal from the second brain wave generator along with a frequency of the audible sound signal from the audible sound generator;
   a first filter connected with the first modulator, for passing, with minimal attenuation, frequency components of the baseband signal up to a low pass filter cutoff frequency, and then rejecting frequency components of other baseband signals above the low pass filter cutoff frequency, from the mixed signals of the first brain wave signal and the audible sound signal modulated from the first modulator to remove undesired noises;
   a second filter connected with the second modulator, for passing, with minimal attenuation, frequency components of the baseband signal up to a low pass filter cutoff frequency, and then rejecting frequency components of other baseband signals above the low pass filter cutoff frequency, from the mixed signals of the second brain wave signal and the audible sound signal modulated from the second modulator to remove undesired noises;
   an audio amplifier connected with the first filter, the second filter and the fetal vital sound generating means, for amplifying both the filtered weak audio frequency signals each generated from the first and second filters and the fetal vital sound signal generated from the fetal vital sound generating means; and
   an audio output means connected with the audio amplifier, for outputting the mixed sound of the amplified audio frequency brain wave sound and fetal vital sound generated from the audio amplifier.

3. The device of claim 1, wherein the fetal vital sound generating means comprises:
   a sound collector for collecting the fetal vital sound signal and generating an electrical signal corresponding thereto;
   an amplifier connected with the sound collector, for amplifying the collected fetal vital sound signal generated from the sound collector to a predetermined signal level; and
   a third filter connected with the amplifier and the audio amplifier, for passing frequency components of the baseband signal up to the detected heartbeat frequency and then rejecting frequency components of other baseband signals above the detected heartbeat frequency, from the amplified fetus vital sound signal generated from the amplifier to remove undesired noises, and outputting the filtered fetus deep sound signal to the audio amplifier of the brain wave sound generating means.

4. The device of claim 1 further comprising:
   a recording/reproducing means connected with the brain wave sound generating means and the fetal vital sound generating means, for recording and reproducing both the filtered audio frequency signal generated from the brain wave sound generating means and the filtered fetal vital sound signal generated from the fetal vital sound generating means.

5. The device of claim 4, wherein the recording/reproducing means comprises:
   a recording amplifier connected with the first and second filters and the audio amplifier of the brain wave sound generating means, and the third amplifier of the fetal vital sound generating means, for amplifying the brain wave sound signal and the filtered audio frequency signal generated from the brain wave sound generating means and the filtered fetal vital sound signal outputted from the fetal vital sound generating means to a predetermined signal level for recording on a recording media in accordance with a recording control signal of a recording key mounted thereto;

a recording/reproducing section connected with the recording amplifier, for recording the amplified the brain wave sound signal and fetal vital sound signal on the recording media therein, and reproducing the recorded brain wave sound signal and fetal vital sound signal from the recording media in accordance with a reproducing control signal; and a controller connected with the recording amplifier and the recording/reproducing means, for controlling the recording and reproducing of the brain wave sound signal and fetal vital sound signal in accordance with the recording and reproducing control signals.

6. The device of claim 1 further comprising:

an output terminal for outputting the brain wave sound signal and the fetal vital sound signal to an external recording/reproducing means.

7. The device of claim 1 further comprising:

a display means coupled to the controller, for displaying a current operating state of the device.

* * * * *